(12) United States Patent
Rudorfer

(10) Patent No.: US 8,993,306 B2
(45) Date of Patent: Mar. 31, 2015

(54) METHOD AND KIT FOR SEPARATING VIRAL AND PROKARYOTIC NUCLEIC ACIDS FROM EUKARYOTIC NUCLEIC ACIDS

(75) Inventor: Walter Rudorfer, St. Oswald/Freistadt (AT)

(73) Assignee: Greiner Bio-One GmbH, Frickenhausen (DE)

( * ) Notice: Subject to any disclaimer, the term of this patent is extended or adjusted under 35 U.S.C. 154(b) by 0 days.

(21) Appl. No.: 13/635,558

(22) PCT Filed: Apr. 7, 2011

(86) PCT No.: PCT/EP2011/055449
§ 371 (c)(1),
(2), (4) Date: Sep. 17, 2012

(87) PCT Pub. No.: WO2011/124653
PCT Pub. Date: Oct. 13, 2011

(65) Prior Publication Data
US 2013/0017552 A1    Jan. 17, 2013

(30) Foreign Application Priority Data
Apr. 8, 2010 (AT) .................................. A 567/2010

(51) Int. Cl.
*C12N 15/10* (2006.01)

(52) U.S. Cl.
CPC .................................. *C12N 15/1003* (2013.01)
USPC ......................................................... 435/270

(58) Field of Classification Search
None
See application file for complete search history.

(56) References Cited

U.S. PATENT DOCUMENTS

| 5,808,041 | A * | 9/1998 | Padhye et al. ................. 536/25.4 |
| 2003/0228600 | A1 * | 12/2003 | Domanico et al. ................ 435/6 |
| 2004/0039188 | A1 * | 2/2004 | Gautsch et al. ............... 536/24.3 |
| 2004/0076980 | A1 * | 4/2004 | Charlton et al. ................... 435/6 |
| 2007/0275378 | A1 | 11/2007 | Werner |
| 2008/0003568 | A1 | 1/2008 | Schmidt et al. |
| 2008/0076912 | A1 * | 3/2008 | Takkellapati et al. ......... 536/25.4 |
| 2008/0187916 | A1 | 8/2008 | Ikonomi et al. |
| 2009/0137024 | A1 | 5/2009 | Stone |
| 2010/0125134 | A1 * | 5/2010 | Lim et al. ...................... 536/23.1 |

FOREIGN PATENT DOCUMENTS

| EP | 1 524 320 | 4/2005 |
| WO | WO 02/26966 | 4/2002 |
| WO | WO2005/085440 | 9/2005 |

OTHER PUBLICATIONS

Prokaryotic and Eukaryotic Cells (see attached, Mar. 12, 2009).*
Dumke (Sensitive Detection of *Mycoplasma pneumoniae* in Human Respiratory Tract Samples by Optimized Real-Time PCR Approach, Journal of Clinical Microbiology, Aug. 2007, p. 2726-2730.*
PCR assay for Mycoplasma detection (hereinafter "WHO"; see attached, Mar. 6, 2008).*
Nascimento et al. (Plasmids in mycoplasma species isolated from goats and sheep and their preliminary typing, Revista de Microbiologia (1999) 30:32-36).*
Sambrook et al. (Isolation of bacteriophage λ and plasmid DNA, in Molecular Cloning: A Laboratory Manual, Cold Spring Harbor Laboratory, Cold Spring Harbor, N.Y., 1982, pp. 90-91).*
Kennedy Plasmid v Genomic DNA Extraction: The Difference, http://bitesizebio.com/1660/plasmid-v-genomic-dna-extractionthe-difference/, Apr. 16, 2009).*
Gnarpe et al., Sample preparation for *Chlamydia pneumoniae* PCR, 1995, pp. 307-308.
Simpson et al., A shuttle system for transfer of YACs between yeast and mammalian cells, Nucleic Acids Research, 1996, vol. 24, No. 23, pp. 4701-4707.
Birnboim and J. Doly. A rapid alkaline extraction procedure for screening recombinant plasmid DNA. Nucleic Acids Research. vol. 7(6); 1979, pp. 1513-1523. Spec. pp. 2 and 15.
Maniatis, T., E. F. Fritsch, and J. Sambrook. 1982. Molecular cloning: a laboratory manual, p. 90-91. Cold Spring Harbor Laboratory, Cold Spring Harbor, N.Y. Spec., p. 2.
Nascimento, Elmiro R., et al. (1999), Plasmid in *Mycoplasma* species from goats and sheep and their preliminary typing. Revista de Microbiologia. 30:32-36 Spec., p. 2.
Andrew D. Bergemann, Jane C. Whitley, and Lloyd R. Finch, Homology of *Mycoplasma* Plasmid pADB201 and *Staphylococcal* Plasmid pE194, J. of Bacteriology, Jan. 1989, p. 593-595 171, No. 1. Spec., p. 2.
John Welsh and Michael McClelland, Nucleic Acids Research, vol. 18, No. 24, pp. 7213-7218, 1990. Spec., p. 12.
Greisen K. et al.; Journal of Clinical Microbiology, Feb. 1994, p. 335-351. vol. 32, No. 2. Spec., p. 13.
J. Sambrook and D.W. Russel. 2001. Molecular cloning: a laboratory manual, Preparation of DNA by Boiling Lysis (pp. 1.43-1.50 and pp. 1.16-1.19), Third Edition, Cold Spring Harbor Laboratory, Cold Spring Harbor, N.Y. Spec., pp. 14 and 18.
International Search Report of PCT/EP2011/055449, date of mailing Jun. 22, 2011.

* cited by examiner

*Primary Examiner* — Christopher M Babic
*Assistant Examiner* — Aaron Priest
(74) *Attorney, Agent, or Firm* — Collard & Roe, P.C.

(57) ABSTRACT

A method for at least partially separating viral and/or prokaryotic nucleic acids from eukaryotic nucleic acids from a biological sample includes re-suspending the cells in the presence of a chelating agent, lysis of the cells by chemical lysis, and/or mechanical lysis, neutralizing the cell lysate and separating the precipitated eukaryotic nucleic acids and obtaining the viral and/or prokaryotic nucleic acids. A kit includes a re-suspension buffer with chelating agent and optionally a saccharide and RNAse, lysis buffer including at least one base and a detergent and neutralizing buffer for at least partially separating viral and/or prokaryotic nucleic acids from eukaryotic nucleic acids from a biological sample. The acid constant of the weak anion defines the pH value and kosmotropic property of the salt (cation+anion) in conjunction with the detergent, which determines the protein solubility and precipitation.

3 Claims, No Drawings

METHOD AND KIT FOR SEPARATING VIRAL AND PROKARYOTIC NUCLEIC ACIDS FROM EUKARYOTIC NUCLEIC ACIDS

CROSS REFERENCE TO RELATED APPLICATIONS

This application is the National Stage of PCT/EP2011/055449 filed on Apr. 7, 2011, which claims priority under 35 U.S.C. §119 of Austrian Application No. A 567/2010 filed on Apr. 8, 2010, the disclosure of which is incorporated by reference. The international application under PCT article 21(2) was not published in English.

The invention relates to a method for at least partially separating viral and prokaryotic nucleic acids from eukaryotic nucleic acids from a biological sample, in particular a cell suspension, comprising the steps of a) centrifuging and re-suspending the eukaryotic cells, b) lysis of the cells, c) neutralizing the cell lysate and d) separating the precipitated eukaryotic nucleic acids, as well as the use of a kit comprising a re-suspension buffer, lysis and neutralizing buffer for at least partially separating viral and prokaryotic nucleic acids from eukaryotic nucleic acids from a biological sample, in particular a cell suspension.

The rapid detection of bacteria and viruses in eukaryotic cells, irrespective of whether in vitro or in vivo, is assuming ever greater importance. Infections in vivo for a human or animal can be life threatening and lead to illnesses, and in vitro, especially in the biopharmaceutical industry, can jeopardize the production of vaccines and biopharmaceutical products in general. Rapid detection of the cause is crucial to correct processing and adjustment to production. However, in order to be able to detect smaller amounts of contamination at an early stage, it is necessary to use very sensitive and also very specific methods. Since it is necessary to detect even the slightest amount of infection or contamination, it is necessary to have an excessive quantity of the material in which the infection or contamination has occurred.

The contamination of cell cultures, for example by mollicutes, is very widespread and is a problem which is taken seriously in biological research and in the biopharmaceutical industry. Contamination by mollicutes, in particular *mycoplasmas*, has very many negative effects on cell cultures, which alter protein synthesis, cell metabolism or cell morphology, for example. As parasitic living bacteria, *mycoplasmas* are the cause of numerous diseases in humans, animals and plants. As a rule, however, bacteria belonging to the class of mollicutes do not kill their host. Instead, they cause chronic infections, which means that they adapt well to the host and thus represent a very successful type of parasitism. In addition to the pathogenic properties of *mycoplasmas*, the infection of cell cultures with *mycoplasmas* plays an important role. Various different methods can be used to detect *mycoplasmas*.

To date, it has been possible to detect mollicute species and the source of mollicute contamination rapidly in cell culture supernatants and media using the product CytoInspect® sold by the applicant, but not in cell suspensions.

From the prior art, "alkaline lysis" is known as a method of isolating plasmid DNA (circular DNA) from bacteria (Birnboim and J. Doly. A rapid alkaline extraction procedure for screening recombinant plasmid DNA. Nucleic Acids Research. Vol. 7(6); 1979 and Maniatis, T., E. F. Fritsch, and J. Sambrook. 1982. Molecular cloning: a laboratory manual, p. 90-91. Cold Spring Harbor Laboratory, Cold Spring Harbor, N.Y.). Alkaline lysis is the standard method used to isolate plasmid DNA from prokaryotic DNA, whereby the prokaryotic DNA is precipitated and the plasmid DNA remains in solution. "Molecular Cloning" also describes how bacterial DNA is denatured using harsh lysis methods (detergents+boiling or alkaline lysis). During lysis, bacterial proteins, cell wall fragments and denatured chromosomal DNA is enclosed in large complexes with the detergent. These complexes can be efficiently precipitated by an exchange of sodium ions with potassium ions. Once the denatured material has been removed, for example by centrifugation, the plasmid DNA is supernatant.

Two other publications (Nascimento R. Elmiro, D. A. (1999), Plasmid in *Mycoplasma* species from goats and sheep and their preliminary typing. Revista de Microbiologia and Andrew D. Bergemann, Jane C. Whitley, and Lloyd R. Finch, Homology of *Mycoplasma* Plasmid pADB201 and *Staphylococcal* Plasmid pE194, J. of Bacteriology, January 1989, P. 593-595 171, No. 1) describe the use of alkaline lysis as a means of separating naturally occurring plasmid DNA in *mycoplasma* from genomic *mycoplasma* DNA, whereby the prokaryotic DNA is separated and only the plasmid DNA remains in solution, as a result of which the prokaryotic (chromosomal) DNA is no longer available for further analysis.

The objective of this invention is to propose a method whereby even small quantities of viral and prokaryotic nucleic acids can be separated from a large volume of eukaryotic cell suspension, in particular with a view to obtaining a detection threshold of <10 cfu/ml (colony forming units/ml) of the bacteria or viruses.

This objective is achieved by the invention, independently in each case, by means of a method for at least partially separating viral and/or prokaryotic nucleic acids from eukaryotic nucleic acids from a biological sample, in particular a eukaryotic cell suspension, comprising the following steps in the following sequence: a) re-suspending the cells in the presence of a chelating agent, in particular EDTA or EDTA in combination with a saccharide, b) lysis of the cells by chemical lysis, such as alkaline lysis, enzymatic lysis and/or boiling lysis and/or mechanical lysis, c) neutralizing the cell lysate and d) separating the precipitated eukaryotic nucleic acids and obtaining the viral and/or prokaryotic nucleic acids; and by the use of a kit comprising a re-suspension buffer with a chelating agent and optionally a saccharide and RNAse, lysis buffer comprising at least one base and a detergent and neutralizing buffer for at least partially separating viral and/or prokaryotic nucleic acids from eukaryotic nucleic acids from a biological sample, in particular a eukaryotic cell suspension. Advantageously, it has been found that eukaryotic DNA, proteins and cell membrane elements are separated, whereas the viral and prokaryotic nucleic acids remain in solution. Since the excess of eukaryotic DNA is separated, a nucleic acid amplification technique (NAAT) can then be undertaken, such as the polymerase chain reaction (PCR) of the recovered nucleic acids. In order to implement nucleic acid amplification techniques (NAAT) successfully, such as PCR for example, it is necessary to have the purest possible DNA or cDNA, etc., as a starting point. Impurities such as proteins, fats or other organic substance or also an excessive amount of foreign DNA (i.e. DNA that must not be amplified) are detrimental to a successful PCR and can even cause total failure. There has also been talk of PCR inhibitors. Tests conducted in the applicant's laboratory showed that foreign DNA in a concentration of ca. >3 µg/PCR prevents the reaction. The smaller the ratio between target DNA and foreign DNA is, the greater the inhibiting effect of the foreign DNA.

Non-conducive target versus foreign DNA ratios are frequently encountered in PCR diagnostics. Examples of this are: PCR from blood, tissue of all types, soil samples, forensic PCR, detection or hygiene inspections in the food or pharmaceutical industry, etc.

The following is an example. In pharmaceutical production, it is a requirement to be able to detect *mycoplasma* contaminations in the order of <10 colony forming units (cfu)/ml from at least 10 ml of cell suspension. The cell count of eukaryotic cells in 10 ml of a fermenter culture is ca. $10^8$ cells. This corresponds to a DNA quantity of ca. 580 μg, in other words a quantity in which PCR no longer takes place. 10 cfu/ml of *mycoplasma* cells in $10^8$ of eukaryotic cells corresponds to a nucleic acid ratio of $1:3\times10^{10}$. Taking a PCR amplified product of 300 nucleotides in length as a basis for calculation, a ratio of $1:10^{14}$ can even be calculated. With such ratios between target and foreign DNA, a PCR amplification is impossible and hence the use of PCR for hygiene inspections from cell suspensions.

The method and kit proposed by the invention have also proved to be of advantage because viral and prokaryotic nucleic acids can be isolated from eukaryotic cell suspensions easily and rapidly and no inhibition takes place either due to cellular proteins or due to cell membrane elements or due to eukaryotic DNA during subsequent amplification. Also of advantage is the fact that intracellular viral and prokaryotic nucleic acids can also be detected.

Re-suspension of the cells may take place directly in the cell suspension and it is preferable to run a centrifugation prior to re-suspension in order to concentrate/pelletize the cells and then re-suspend them. The re-suspension takes place in the presence of a chelating agent, in particular EDTA, and optionally a saccharide, in which case the chelating agent destabilizes the cell membrane and inhibits DNAses. Saccharide stabilizes the osmolarity.

The lysis may be implemented by chemical lysis, such as alkaline lysis, enzymatic lysis, and/or boiling lysis and/or mechanical lysis, as a result of which, in addition to intranuclear nucleic acids, cytoplasmic nucleic acids can also be isolated.

Lysis preferably takes place in the presence of a detergent, in particular SDS, and a base, the detergent perforating the cell membrane and the base loosening the cell wall and releasing and denaturing nucleic acids. Cellular DNA is linearized, whereas circular DNA remains unchanged.

Neutralization takes place in the presence of at least one salt or a substance which reduces the solubility of proteins, in particular a kosmotropic salt, in particular potassium or sodium acetate or ammonium sulfate, so that circular DNA can be re-natured whereas cellular DNA remains denatured in the form of single-strand nucleic acid and precipitates. In an alternative embodiment, neutralization may also take place in the presence of a chaotropic salt, in particular a guanidinium salt, such as guanidinium hydrochloride. The eukaryotic cell elements, proteins and eukaryotic genomic nucleic acids precipitate out and can be separated by means of centrifugation, for example.

The viral and prokaryotic nucleic acids remain in solution and are cleaned after being neutralized, in particular precipitated (e.g. alcohol precipitation or column cleaning—NucleoSpin® Plasmid), so that the nucleic acids are present in the form of cell pellets or eluted from the column in a clean state, after which the other work steps such as amplification, in particular PCR, can be implemented.

Also of advantage is the fact that by amplifying the prokaryotic nucleic acids from a cell suspension with a cell density of $10^5$ to $10^{10}$ cells/ml, a detection threshold of <10 cfu/ml or <10 copies/ml can be obtained, thereby resulting in a very sensitive method of detecting contamination of viruses and prokaryotes in eukaryotic cells, in particular human and animal cells and cell cultures. Another advantage is that viral and prokaryotic nucleic acids can be detected from up to 100 ml of cell suspension. The ratio of the number of prokaryotic or viral target DNA to the number of disruptive eukaryotic DNA molecules always has a ratio of <1, in particular by several orders of magnitude.

In the case of one possible embodiment of the invention, mollicute DNA can be separated from eukaryotic DNA by the "alkaline lysis" method, whereby cellular components and the DNA of eukaryotic cells can advantageously be separated to the degree that there is no negative effect for either the subsequent extraction or amplification.

It has also proved to be of advantage that, in conjunction with NAAT, it is possible to detect mollicutes, in particular *mycoplasmas*, in a concentration of less than 5 cfu/ml from a cell suspension with a cell density of up to $10^{10}$ eukaryotic cells/ml or 5 cfu/ml *mycoplasmas* from 100 ml of a cell suspension with $10^9$ cells or 10 ml with $10^8$ cells.

The advantages of using the kit proposed by the invention correspond to the advantages of the method proposed by the invention described above.

In the context of the invention, biological sample should be understood as meaning cellular material which can be isolated from nucleic acid, in particular cells from cell culture, cell lines, cells from blood, urea, saliva or other body fluids, as well as cells from tissue, e.g. biopsies, swabs, etc.

As proposed by the invention, nucleic acids, in particular viral or prokaryotic DNA of an organism, is separated from the DNA of a eukaryotic organism. Viral and prokaryotic intra- or extracellular DNA of an organism is packaged, i.e. structures or casings are provided.

The expression "alkaline lysis" should be understood as meaning the method of isolating intracellular plasmid DNA from bacteria mentioned above. Plasmid DNA is naked, i.e. it has no protein casing. As proposed by the invention, this method is used with adaptations in order to separate viral and/or prokaryotic nucleic acids from eukaryotic nucleic acids from eukaryotic cell suspensions. Surprisingly, it was possible to demonstrate that eukaryotic nucleic acids can be separated from prokaryotic or viral nucleic acids, which remain in solution, whereas according to the relevant literature, prokaryotic DNA is separated using the "alkaline lysis" method and only the plasmid DNA remains in solution.

During various tests, some of which will be described below, it was demonstrated that it was possible to detect *mycoplasma* DNA from suspension cultures but only from a detection threshold of 500 cfu/ml.

Using the DNA separating system, Looxster® Universal kit, prokaryotic DNA can be isolated from a DNA mixture. This kit enables prokaryotic DNA to be separated from a mixture containing eukaryotic DNA. To this end, a process of affinity chromatography is applied, during which the non-methylated DNA units of the bacterial DNA are bound by a protein and thus isolated. Due to the high DNA separation, confirmed by photometric measurement values (ca. 7% of the original DNA content remains after processing the sample with the Looxster®), DNA losses occur. The high loss of DNA during processing with the LOOXSTER® explains why three types (*mycoplasma gallisepticum, mycoplasma fermentans* and *mycoplasma hyorhinis*) cannot be detected until 500 cfu/ml.

In the case of another extraction method used to isolate *mycoplasma* DNA from suspension cultures, NP 40 (Tergitol type NP-40 (nonyl phenoxylpolyethoxylethanol)) was tested.

NP-40 should break open the cytoplasma membrane of *mycoplasmas* and eukaryotic cells. The core membrane of the eukaryotic cells should remain intact. *Mycoplasma* DNA is located in the cytoplasm and eukaryotic DNA in the cell core. NP-40 should release the *mycoplasma* DNA whilst the eukaryotic DNA remains in the cell core, thereby enabling the DNA to be separated. In practice, however, the opposite effect was found. The number of *mycoplasmas* in the cell pellet and in the cell supernatant is approximately the same. If the NP-40 had actually worked, the concentration of *mycoplasmas* in the supernatant would have been significantly higher. Consequently, it is not possible to separate *mycoplasma* DNA and eukaryotic DNA using NP-40.

The possibility of separating mollicute DNA from humans and human cell cultures by means of filters was also tested, but the *mycoplasmas* were not retained by the filter even though the eukaryotic cells were relatively large already. However, large quantities of cells block the membrane.

The possibility of separating *mycoplasmas* from eukaryotic cells by centrifugation was also evaluated (eukaryotic cells should be heavier than *mycoplasmas*). The disadvantage of this approach was found to be that intracellular *mycoplasmas* cannot be detected and the sensitivity is therefore low.

By contrast with the prior art where plasmids are separated from prokaryotic DNA, viral and prokaryotic nucleic acids are separated from eukaryotic DNA using the method proposed by the invention. In addition to the difference of prokaryotes/eukaryotes, the size ratio of the DNA separated (for example mollicutes, in particular *mycoplasmas*, DNA of eukaryotic DNA) is significantly different from the ratio known from the prior art if using the method proposed by the invention. Although mollicute chromosomes, in particular *mycoplasma* chromosomes, are smaller by ca. a factor of 3-5 than those of *E. coli*, this difference in size is not so great compared with *E. coli* (from which the most plasmids are obtained) that *mycoplasma* chromosomes would behave like plasmids. Plasmids are usually smaller than *E. coli* genomes by a factor of 50-100. And in the case of two mollicute species, acholeplasma laidlawii and spiroplasma citri, the ratio of the genome size to that of *E. coli* is even a factor of only 2-3.

Genome sizes of individual bacteria species are set out below by way of example.

| Species | Genome size [kb] |
|---|---|
| Acholeplasma laidlawii | 1680 |
| Spiroplasma citri | 1820 |
| Streptococcus mutans NN2025 | 2013 |
| Staphylococcus epidermidis ATCC 12228 | 2499 |
| Staphylococcus haemolyticus JCSC1435 | 2685 |
| Enterococcus faecalis OG1RF | 2739 |
| Clostridium difficile CD196 | 4110 |
| Bacillus subtilis | 4214 |
| Escherichia Coli | 4557 |
| Mycoplasma spp. | 580-1358 |

The method and kit proposed by the invention may be used, for example, to separate bacterial, in particular prokaryotic, DNA of the bacteria types *Staphylococcus haemolyticus, Clostridium difficile, Streptococcus mutans, Staphylococcus epidermidis, Lactobacillus casei, Enterococcus faecalis, Staphylococcus saprophyticus, Streptococcus mitis, Eubacterium nodatum, Bacillus subtilis, Streptococcus gordonii, Enterococcus faecium, E. coli, Peptostreptococcus micros, Streptococcus agalactiae, Streptococcus oralis, Streptococcus pneumoniae, Streptococcus pyogenes, Veillonella parvula*, from eukaryotic DNA. It would naturally also be possible to separate the DNA of other types of bacteria from eukaryotic DNA.

The method and kit proposed by the invention may also be used to separate prokaryotic DNA from eukaryotic DNA from human or other eukaryotic cells. For example, the bacterial DNA of *Clostridium perfringens, Enterococcus faecalis, Enterococcus faecium, Listeria monocytogenes, Propionibacterium acnes, Staphylococcus aureus, Staphylococcus epidermidis, Streptococcus agalactiae, Streptococcus dysgalactiae, Subspecies equisimilis, Streptococcus pneumoniae, Streptococcus pyogenes, Coagulase negative Staphylococcus, Acinetobacter baumannii, Enterobacter aerogenes, Enterobacter cloacae, Escherichia coli, Haemophilus influenzae, Kingella kingae, Klebsiella oxytoca, Klebsiella pneumoniae, Neisseria meningitidis, Proteus mirabilis, Proteus vulgaris, Pseudomonas aeruginosa, Salmonella enterica* subspecies *enterica, Serratia marcescens, Stenotrophomonas maltophilia, Bacteroides fragilis, Campylobacter jejuni, Campylobacter coli, Enterobacteriaceae, Neisseria* sp. non-meningitidis, *Bacteroides fragilis, Bacteroides vulgatus, Bacteroides thetaiotaomicron;* Coagulase negative *Staphylococcus; S. haemolyticus, S. hominis S. lugdunensis, S. saprophyticus, S. warneri, S. xylosus;* Enterobacteriaceae: *Citrobacter amalonaticus, Citrobacter braakii, Citrobacter freundii, Citrobacter koseri, Enterobacter hormaechei, Enterobacter sakazakii, Kluyvera intermedia, Morganella morganii, Pantoea agglomerans, Providencia rettgeri, Providencia stuartii, Yersinia enterocolitica, Yersinia pseudotuberculosis; Neisseria* sp. non-meningitidis: *N. gonorrhoeae, N. subflava, N. sicca, N. cinerea, N. elongata* subspecies *nitroreducens, N. flavescens, N. lactamica, N. zoodegmatis; Salmonella enterica* subspecies *enterica* serovars: *Enteritidis, Oranienburg, Othmarschen, Panama, Paratyphi, Stanley, Typhi, Typhimurium*, and *Virchow* group A,B,C,D could also be separated from human or other eukaryotic genomic DNA.

Another example of how the method and kit proposed by the invention might be used is that of separating viral DNA, such as retroviruses, herpes viruses, flaviviruses, papovaviruses, paramyxoviruses, parvoviruses, picornaviruses, caliciviruses, rhabdoviruses, reoviruses, togaviruses, in particular viruses such as influenza, parainfluenza, Sindto virus, bovine viral diarrhea, murine leukemia, West Nile virus, human immunodeficiency, human papilloma, bovine herpes, bovine biral diarrhea, pseudo rabies, reo 3, encephalomyocarditis, hepatitis A, hepatitis B, hepatitis C, polio type 1, Simian 40 (SV-40), minute virus of mice, vesicular stomatitis, porcine parvo, avian leukosis, Epstein Barr virus, herpes simplex, encephalitis, cytomegalo, vesivirus 2117, etc., from eukaryotic DNA.

Possible examples of eukaryotic DNA, in addition to human and animal genomic DNA, are also cell lines, which are used in biotechnology or the biopharmaceutical industry. Examples of such cell lines are AS-30D, MDCK, MCF-7, MFM-223, HCC1937, KPL-1, T-47D, UM-UC-3, TCC-SUP, J82, T-24, Vm-Cub 1, HL-60, PL21, THP-1, Molt-4, NALM-1, WSU-NHL, DOHH-2, SU-DHL-4, U-251 MG, U373 MG, U-87 MG, SNB-19, DAOY, D425, D341, UW 228-2, HEP-G2, 1184, A-431, CaCo-2, HaCaT, HEK 293, HEK 293 EBNA, HeLa, Huvec-c, HDMEC, MG-63, RPMI-2650, SaOs-2, HP-6017, GT2, BHK-21, C2C12, CHO-K1, CHO-XM, COS-1, CS-1, L cells, MC3T3-E1, MDCK, mocha, NIH-3T3, PC12, PK-1, REF52, etc. Naturally, it would also be possible to separate the DNA of other cell lines from viral and prokaryotic nucleic acid.

Example 1

An example of the method proposed by the invention will be explained below. Mollicute DNA, especially *Achole-*

*plasma* (*A.*) *axanthum, A. laidlawii, A. modicum, A. morum, A. oculi, A. vituli, Mycoplasma* (*M.*) *alkalescens, M. arginini, M. arthritidis, M. bovigenitalium, M. bovirhinis, M. bovis, M. bovoculi, M. buccale, M. californicum, M. canadense, M. canis, M. eqhirhinis, M. faucium, M. fermentans, M. flocculare, M. gallinaceum, M. gallinarum, M. gallisepticum, M. genitalium, M. glycophilium, M. hominis, M. hyopharyngis, M. hyopneumoniae, M. hyorhinis, M. hyosynoviae, M. orale, M. pirum, M. pneumoniae, M. pulmonis, M. salivarium, M. synoviae, S. citri, S. kunkelii, U. diversum/urealyticum*, is extracted from an AS-30D cell suspension with a cell density of $10^7$ cells/ml and a detection threshold of 5 cfu/ml obtained.

Ten ml of cell suspension are centrifuged for 20 minutes at 4500 g and 20° C. The supernatant is discarded and the cell pellet re-suspended by vortexing. 500 µl of re-suspension buffer (50 mM Glucose, 25 mM Tris/HCl pH 8.0, 10 mM EDTA) including 20 µl of internal PCR control (synthetic plasmid, which has primer binding points to the PCR primers, but which otherwise (apart from the capture sonde) may have any totally random sequence) are then added and vortexed. A quantity of 20 µl of proteinase K (23 mg/ml) is added, followed by vortexing.

In the next step, 500 µl of lysis buffer (10 ml 0.2 N NaOH, 10% SDS) are added, followed by careful pivoting, incubation for 10 minutes at 56° C. and then centrifugation for 1 minute at 4500 g and 20° C. This makes use of the effect whereby prokaryotes (*mycoplasmas*) have circular DNA and eukaryotes have linear DNA.

600 µl of neutralizing buffer (3 M Na acetate, pH 4.8 to 5.2) are then added, followed by careful pivoting and centrifugation for 1 minute at 4500 g. The supernatant is transferred to a new test tube and centrifuged again for 10 minutes at 11,000 g at least.

The DNA can then be isolated from the supernatant by means of a column, such as a silicate column for example, and eluted from the column and recovered by means of an isopropanol precipitation. By using the method and volume of buffer described above, the cellular components are already separated as far as possible, which also advantageously then makes it easier to extract the DNA, for example because clogging of the der columns can be prevented.

A PCR is then implemented with specific primers for mollicutes, in a manner known from the prior art (e.g. the Cyto-Inspect® kit sold by the applicant, Cat. No. 464 060), the amplified product hybridized on a microarray and then detected and the result analyzed.

The table below sets out the result of detecting mollicutes using the method of extracting the DNA followed by PCR amplification of the eluate described under Example 1. The SNR data (signal to noise ratio) for five important mollicute strains is given.

Two different media, firstly RPMI cell culture medium without cellular components such as proteins and cell fragments, and secondly 10 ml of AS-30D cell suspension with a cell quantity of $10^8$ cells, are compared. With 5 cfu/ml, clear signals can be detected. Two sets of results from independent experiments (1 respectively 2) are given in each case. The result demonstrates that the PCR is sensitive, even with large volumes and complex samples containing high quantities of eukaryotic DNA and proteins. The AS-30D cell line is also representative of other cell lines.

Using the example described above, it is possible to obtain a detection threshold of 5 cfu/ml. A minimum of 10 cfu/ml is required by the European Pharmacopoeia.

Example 2

In the following example, *Staphylococcus aureus, Staphylococcus epidermidis*, Coagulase negative *Staphylococcus: S. haemolyticus, S. hominis S. lugdunensis, S. saprophyticus, S. warneri, S. xylosus* from the MDCK cell culture line are detected with a cell suspension containing $10^8$ cells/ml. A detection threshold of 5 cfu/ml is obtained.

Twenty ml of cell suspension are centrifuged for 15 minutes at 4000 g and 22° C. The supernatant is discarded and the cell pellet re-suspended by vortexing. 400 µl of re-suspension buffer (1 M Tris HCL pH 8.0, 0.5 M EDTA pH 8.0, 10 mg/ml RNAseA) including 10 µl of internal PCR control are then added and vortexed.

In the next step, 500 µl of lysis buffer (2 M KOH, 20% CHAPS) are added and carefully pivoted, incubated for 10 minutes at 56° C. and then centrifuged for 1 minute at 4500 g and 20° C.

600 µl of neutralizing buffer (5M potassium acetate, glacial acetic acid, end result is a 3 M potassium and 5M acetate concentration) are then added and carefully pivoted and centrifuged for 1 minute at 4500 g. The supernatant is transferred to a new test tube and centrifuged again for 10 minutes at 11,000 g at least.

As with the first example, the DNA is then eluted, amplified with primers specific for *Staphylococcus* infections (John Welsh and Michael McClelland, Nucleic Acids Research, Vol. 18, No. 24, 7213, 1990), the amplified product hybridized on a microarray and the result detected and analyzed.

Example 3

In the following example, *Neisseria meningitidis* from human mucous cells with a cell density von $10^6$ cells/ml is detected. A detection threshold of 5 cfu/ml is obtained.

One hundred ml of cell suspension are centrifuged for 15 minutes at 4000 g and 22° C. The supernatant is discarded and the cell pellet re-suspended by vortexing. 500 µl of re-suspension buffer (50 mM Glucose, 25 mM Tris/HCl pH 8.0, 10 mM EDTA, 10 mg/ml RNAseA) including 20 µl of internal PCR control are then added and vortexed.

|  | Mycoplasma orale | | Acholeplasma laidlawii | | Mycoplasma pneumonia | | Mycoplasma fermentano | | Mycoplasma hyorhinis | | Spiroplasma citrii/kunkelii | |
|---|---|---|---|---|---|---|---|---|---|---|---|---|
|  | 1 | 2 | 1 | 2 | 1 | 2 | 1 | 2 | 1 | 2 | 1 | 2 |
| AS-30D | 993 | 899 | 725 | 713 | 1601 | 1282 | 116 | 142 | 214 | 120 | 320 | 108 |
| RPMI | 1208 | 653 | 931 | 723 | 1424 | 1617 | 432 | 441 | 240 | 190 | 618 | 128 |

In the next step, 500 µl of lysis buffer (2 M NaOH, 20% SDS) are added and carefully pivoted, incubated for 10 minutes at 56° C. and then centrifuged for 1 minute at 4000 g and 20° C.

600 µl of neutralizing buffer (3 M Na acetate pH 4.8 to 5.2) are then added and carefully pivoted and centrifuged for 1 minute at 4000 g. The supernatant is transferred to a new test tube and centrifuged for another 10 minutes at 10,000 g at least.

As with the first example, the DNA is then eluted, amplified with specific primers for *Neisseria meningitidis* (Greisen K. et al.; Journal of Clinical Microbiology, February 1994, p. 335-351), the amplified product hybridized on a microarray and the result detected and evaluated.

Example 4

Human Papilloma virus from the human cell line LC5 with a cell density of 10^9 cells/ml are detected. A detection threshold of 5 copies/ml is obtained.

Fifty ml of cell suspension are centrifuged for 20 minutes at 4500 g and 20° C. The supernatant is discarded and the cell pellet re-suspended by vortexing. 500 µl of re-suspension buffer (100 mM Tris/HCl pH 8.0, 10 mM DMSA) including 20 µl of internal PCR control are then added and vortexed.

In the next step, 500 µl of lysis buffer (1M LiOH, 1% Triton-X 100) are added and carefully pivoted, incubated for 10 minutes at 56° C. and then centrifuged for 1 minute at 4500 g and 20° C.

600 µl of neutralizing buffer (4 M K-phosphate) are then added and carefully pivoted and centrifuged for 1 minute at 4000 g. The supernatant is transferred to a new test tube and centrifuged for another 10 minutes at 15,000 g at least.

The DNA is then precipitated by means of alcohol precipitation, hybridized with specific primers as disclosed in EP 2 062 983 A2 and the result detected and analyzed.

Example 5

Vesivirus from the human cell line HEK with a cell density of 10^9 cells/ml is detected. A detection threshold of 10 copies/ml is obtained.

One hundred ml of cell suspension are centrifuged for 20 minutes at 4500 g and 20° C. The supernatant is discarded and the cell pellet re-suspended by vortexing. 500 µl of resuspension buffer (100 mM Tris/HCl pH 8.0, 10 mM DMPS) including 20 µl of internal PCR control are then added and vortexed.

In the next step, the cells are broken open by boiling lysis (J. Sambrook and D. W. Russel. 2001. Molecular cloning: a laboratory manual, Preparation of DNA by Boiling Lysis (1.43 and A1.16), Third Edition, Cold Spring Harbor Laboratory, Cold Spring Harbor, N.Y.) and then centrifuged for 1 minute at 4500 g and 20° C.

600 µl of neutralizing buffer (4 M K-phosphate are then added and carefully pivoted and centrifuged for 1 minute at 4000 g. The supernatant is transferred to a new test tube and centrifuged for another 10 minutes at 15,000 g at least.

The DNA is then recovered by means of caesium chloride centrifugation, amplified with specific primers for Vesivirus (ViralSEQ™ Vesivirus Assay), the amplified product hybridized on a microarray and the result detected and analyzed.

A few possible compositions for the buffers which may be used for the purpose of the invention are listed by way of example below:

re-suspension buffer:
50 mM glucose, 25 mM Tris/HCl pH 8.0, 10 mM EDTA or
1 M Tris HCL pH 8.0, 0.5 M EDTA pH 8.0, 10 mg/ml RNAseA or
50 mM glucose, 25 mM Tris/HCl pH 8.0, 10 mM EDTA, 10 mg/ml RNAseA lysis buffer:
10 ml 0.2 N NaOH, 10% SDS or
2 M NaOH, 20% SDS or
0.2 N NaOH, 1% SDS
neutralizing buffer:
3 M Na acetate pH 4.8 to 5.2 or
5M potassium acetate, glacial acetic acid, end result is a 3 M potassium and 5M acetate concentration Instead of using the method specifically described in examples 1 to 4, the bacterial or viral DNA or RNA may also be separated from eukaryotic nucleic acids by means of the following method, in which case a detection threshold of 10 cfu/ml or 10 copies/ml is obtained. 1. Bacterial culture pelletization, 2. re-suspension in ice-cold alkaline lysis solution I (or lysozyme, see Birnboim and Doly 1979), 3. add alkaline lysis solution II, store on ice, 4. add alkaline lysis solution III, store on ice, 5. centrifuge at 4° C., recover supernatant, 6, optional phenol-chloroform extraction, 7. recover the viral or bacterial DNA by the steps comprising a. precipitating the DNA or RNA with ethanol or isopropanol, b. centrifuging, c. removing the supernatant, d, repeating steps a-c, e. removing the residual ethanol by air drying, f. placing the plasmid DNA in TE buffer (pH 8.0) and RNAse A. Alkaline lysis solution I is made up of 50 mM glucose, 25 nm Tris-Cl (pH 8.0), 10 nM EDTA (pH 8.0), alkaline lysis solution II is made up of 0.2 N NaOH, 1% (w/v) SDS and alkaline lysis solution III is made up of 5M potassium acetate, glacial acetic acid (end result is a 3 M potassium and a 5 M acetate concentration).

The following method is an alternative to the method just described above and hence to the method described in examples 1 to 4. It is less harsh and therefore causes less damage to the bacterial or viral DNA and RNA but also has a lower yield, as a result of which the detection threshold also drops. The bacterial culture is firstly pelletized and re-suspended in a Tris-sucrose solution. In the subsequent steps, lysozyme with 0.25 M EDTA (pH 8.0) is added, 10% SDS is added, NaCl (final concentration 1 M) is added and the bacterial or viral DNA and RNA recovered by the steps comprising: a. removing the high-molecular DNA and bacterial "debris" by centrifugation, recovering the supernatant, b. 1× phenol-chloroform extraction and 1× chloroform extraction, c. ethanol precipitation of the aqueous phase, d. centrifugation and washing (70% ethanol), drying, g. placing the plasmid DNA in TE buffer (pH 8.0).

In alternative embodiments, however, other buffer compositions and other methods may be used for the lysis, as explained above.

For example, for the re-suspension, a chelating agent other than EDTA may be used, such as for example DMSA, DMPS, etc., although not all chelating agents are compatible with all bases because virtually all divalent cations form insoluble complexes with EDTA and the EDTA quantity would immediately be used up by the base. The choice of chelating agent can improve the lysis.

Apart from alkaline lysis, other lysis methods may also be used for the lysis, such as boiling lysis, enzymatic lysis and mechanical lysis. The relevant parameters in the case of alkaline lysis are the base, which enables a specific pH value to be obtained, and the choice and concentration of detergent. Apart from NaOH, KOH may also be used as a base, for example. However, other bases such as LiOH, RbOH, CsOH, Ca(OH)$_2$, Sr(OH)$_2$, Ba(OH)$_2$ may also be used. Alternatively, other organic bases may be used for cell lysis, such as bases containing nitrogen, for example.

Amongst other things, the detergent used will largely depend on the type of cell to be lysed. The detergent may be both an ionic detergent such as SDS or deoxycholic acid, as well as a zwitterionic detergent such as CHAPS (3-[(3-cholamidopropyl)dimethylammonio]-2-hydroxy-1-propane sulfonate) or a non-ionic detergent such as Triton-X, Nonidet P40 (NP-40), n-octylglucoside as well as ethyltrimethyl ammonium bromide or cetyltrimethyl ammonium bromide (CTAB). Possible concentrations of the ionic detergent in the lysis buffer lie between 0.01 and 0.5% and in the case of non-ionic detergent between 0.1 and 2%.

A significant role may also be ascribed to the cation exchange from sodium to potassium of dodecyl sulfate (if the neutralizing buffer contains potassium ions), which is much less readily soluble. The solubility of potassium dodecyl sulfate (KDS) is much lower than that of sodium dodecyl sulfate (SDS=sodium dodecyl sulfate). Adding potassium acetate causes the much less soluble KDS to precipitate For the neutralizing process where proteins precipitate, one theory would be that separating eukaryotic DNA from viral and prokaryotic nucleic acid, in particular DNA, would primarily be based on this step because eukaryotic DNA precipitates together with the DNA-bound proteins, whereas prokaryotic DNA to which no/only few proteins are bound does not precipitate.

There are essentially three parameters which would affect separation of eukaryotic DNA from prokaryotic DNA: 1. pH value, 2. kosmotropic effect which controls precipitation and 3. the detergent.

The first two parameters are controlled on the basis of the choice of salt for the neutralizing buffer. The acid constant of the weak anion defines the pH value and kosmotropic property of the salt (cation+anion) in conjunction with the detergent, which determines the protein solubility and precipitation. The pH value could also affect the solubility of the nucleic acids. The solubility of proteins is at its lowest at the isoelectric point (IP) and the pH value for the protein precipitation must therefore be set so that it is as close to the IP as possible. The effect of kosmotropic salts is usually enhanced if the pH value is lower than the IP.

There are a few standard methods (salting out) for precipitating/cleaning the proteins, such as trichloroacetic acid (TCA) precipitation or ammonium sulfate precipitation, and fractionation can also be obtained on the basis of a sequential change, e.g. ammonium concentration. The salts may be chosen on the basis of the Hofmeister Series, which changes from kosmotropic to chaotropic from left to right. Kosmotropic salts stabilize proteins and hydrophobic aggregates in solution, whereas they reduce the solubility of hydrophobic aggregates. They therefore make proteins less soluble (similar to the ammonium sulfate protocol).

The kosmotropic effect (=salting out, reduction in solubility) is even further enhanced if the temperature is reduced.

The lower the protein concentration in the solution is, the higher the concentration of salt necessary to cause salting out. (However, this does not apply to all proteins). In the neutral or slightly acid range, it is preferable to work with high concentrations of NaCl (5.3 M), $Na_2SO_4$ (1.9 M), $(NH_4)_2SO_4$ (4M) at different temperatures (0-25° C.) to a certain extent. $MgSO_4$, Na- or K-phosphate (3-3.7 M), Na-acetate may also often be used as a first precipitation step for pre-cleaning.

Other reagents for cell lysis may be used in the following concentrations: the salt concentration is usually between 0 and 1M and the concentration of divalent cations is between 0 and 10 mM and the EDTA concentration between 0 and 5 mM. The pH value is usually between 4.0 and 14.0.

Cleaning the DNA, such as by alcohol precipitation (ethanol, isopropanol, etc.), precipitation with polyethylene glycol, caesium chloride centrifugation or column cleaning (column chromatography), at the end of the method proposed by the invention may be important in terms of removing inhibitors but is not essential for separating viral and prokaryotic nucleic acids, in particular DNA, from eukaryotic DNA, which takes place beforehand already.

To enable small nucleic acid fragments to be removed, a centrifugation process may be run with NaCl (J. Sambrook and D. W. Russel. 2001. Molecular cloning: a laboratory manual, Third Edition, Cold Spring Harbor Laboratory, Cold Spring Harbor, N.Y. 1.78). Plasmid DNA preparations are often contaminated by small nucleic acid fragments (RNA and DNA), which may originate from bacterial chromosomes or broken plasmids. Although their weight is low, they can be high in number. The absence of these fragments is desirable if the plasmid DNA has to be sequenced or amplified with PCR. Other methods used to remove small nucleic acid fragments are Sephacryl S-1000 chromatography and precipitation with lithium chloride (LiCl). LiCl is a strong dehydrating agent which reduces the solubility of RNA and removes proteins from chromatin (Kondo et al. 1979), which means that contaminations of high-molecular RNA and proteins can be removed from the plasmid preparation by precipitation.

In addition to the steps of obtaining the sample and extracting DNA, detecting mollicutes also involves the steps of amplification by means of PCR, hybridization, washing, scanning and analyzing the result using CytoInspect® sold by Greiner Bio-One GmbH.

Viral and prokaryotic nucleic acids can also be separated from vegetable and fungal DNA, in which case it is necessary to run other lysis steps before or in addition to the alkaline lysis, for example a mechanical lysis. The biological sample, in particular a cell suspension, is resuspended with the resuspension buffer and neutralizing buffer added to the lysate so that the vegetable and fungal DNA can be separated using the method proposed by the invention.

On what theoretical principles the process of separating viral and prokaryotic nucleic acid, in particular DNA, from eukaryotic DNA, as proposed by the invention is based had not yet been fully explained. As mentioned above, possible explanations might be the size, linearity and protein coupling of eukaryotic DNA.

In addition to separating viral and prokaryotic nucleic acid from eukaryotic nucleic acid as described above, it is also possible to detect viral and prokaryotic nucleic acid in cell culture supernatants, cell culture media, protein-rich samples with high BSA-concentrations and allantoic fluid (hen's egg).

All the figures relating to ranges of values in the description should be construed as meaning that they include any and all part-ranges, in which case, for example, the range of 1 to 10 should be understood as including all part-ranges starting from the lower limit of 1 to the upper limit of 10, i.e. all part-ranges starting with a lower limit of 1 or more and ending with an upper limit of 10 or less, e.g. 1 to 1.7, or 3.2 to 8.1 or 5.5 to 10.

The embodiments described as examples represent possible variants of the method proposed by the invention and use of the kit, and it should be pointed out at this stage that the invention is not specifically limited to the variants specifically illustrated, and instead the individual variants may be used in different combinations with one another and these possible variations lie within the reach of the person skilled in this technical field given the disclosed technical teaching. Accordingly, all conceivable variants which can be obtained by combining individual details of the variants described and illustrated are possible and fall within the scope of the invention.

The objective underlying the independent inventive solutions may be found in the description.

The invention claimed is:

1. A method for separating genomic prokaryotic DNA of Mollicutes from chromosomal eukaryotic DNA from a biological sample, comprising the following steps in the following order:
    a) centrifugation of a eukaryotic cell suspension with a cell density of up to $10^{10}$ cells/ml and re-suspending the cells in the presence of chelating agent EDTA,
    b) lysis of the cells by chemical lysis in the presence of a detergent SDS and base NaOH,
    c) neutralizing the cell lysate in the presence of at least one salt sodium potassium acetate, and
    d) separating precipitated eukaryotic DNA and obtaining the prokaryotic genomic DNA by silica column chromatography, wherein a detection threshold of <10 cfu/ml or <10 copies/ml is obtained by amplifying the genomic prokaryotic separated DNA from the eukaryotic cell suspension with a cell density of up to $10^{10}$ cells/ml.

2. The method according to claim 1, wherein viral and prokaryotic nucleic acids are cleaned after having been neutralized.

3. The method according to claim 1, wherein a detection threshold of 5 colony forming units for mollicutes in a 10 ml cell suspension with a cell count of $10^{8}$ cells is obtained.

* * * * *